United States Patent
Jeon et al.

(10) Patent No.: US 10,976,224 B2
(45) Date of Patent: Apr. 13, 2021

(54) CELL PATTERNING MATERIAL, PREPARATION METHOD THEREOF, AND USE THEREOF

(71) Applicant: KOREA INSTITUTE OF SCIENCE AND TECHNOLOGY, Seoul (KR)

(72) Inventors: Hojeong Jeon, Seoul (KR); Indong Jun, Seoul (KR); Kangwon Lee, Seoul (KR); Hyung-Seop Han, Seoul (KR); Jimin Park, Seoul (KR); Myoung-Ryul Ok, Seoul (KR); Yu Chan Kim, Seoul (KR); Hyun Kwang Seok, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 498 days.

(21) Appl. No.: 15/753,115

(22) PCT Filed: Aug. 24, 2016

(86) PCT No.: PCT/KR2016/009377
§ 371 (c)(1),
(2) Date: Feb. 15, 2018

(87) PCT Pub. No.: WO2017/034316
PCT Pub. Date: Mar. 2, 2017

(65) Prior Publication Data
US 2018/0238780 A1  Aug. 23, 2018

(30) Foreign Application Priority Data
Aug. 24, 2015 (KR) .................. 10-2015-0118868

(51) Int. Cl.
*G01N 1/31* (2006.01)
*C12N 5/00* (2006.01)
(Continued)

(52) U.S. Cl.
CPC ............ *G01N 1/31* (2013.01); *B01J 19/0046* (2013.01); *G01N 33/5005* (2013.01);
(Continued)

(58) Field of Classification Search
None
See application file for complete search history.

(56) References Cited

U.S. PATENT DOCUMENTS

| 7,541,187 B2 * | 6/2009 | Myles .................... C12M 25/14 435/320.1 |
| 2009/0248145 A1 * | 10/2009 | Chan .................... C12N 5/0691 623/1.41 |
| 2014/0242632 A1 | 8/2014 | Kim et al. |

FOREIGN PATENT DOCUMENTS

| KR | 10-2013-0042857 A | | 4/2013 | |
| WO | WO 2007/087402 | * | 8/2007 | .............. C12M 3/00 |

OTHER PUBLICATIONS

Definition of "Patterned" from Cambridge Dictionary. Retrieved from URL: https://dictionary.cambridge.org/us/dictionary/english/patterned on Oct. 8, 2020 (Year: 2020).*

(Continued)

*Primary Examiner* — Allison M Fox
(74) *Attorney, Agent, or Firm* — Birch, Stewart, Kolasch & Birch, LLP

(57) ABSTRACT

A cell patterning material, a method of preparing the cell patterning material, a cell patterning method using the cell patterning material, and a biosensor including patterned cells obtained by using the cell patterning method are provided. According to the present disclosure, cells may be conveniently and efficiently patterned and the time for applying external stimulation for patterning may be controlled. In addition, the patterned cells may have an excellent proliferation rate and excellent differentiation efficiency, and (Continued)

may be re-patterned in a different direction, and High-throughput screening using the patterned cells is possible.

18 Claims, 14 Drawing Sheets

(51) Int. Cl.
 *B01J 19/00* (2006.01)
 *G01N 33/50* (2006.01)
(52) U.S. Cl.
 CPC ........ *C12N 5/0068* (2013.01); *C12N 2533/74* (2013.01); *C12N 2535/10* (2013.01)

(56) References Cited

OTHER PUBLICATIONS

Soleas et al, Biomaterials Science, 2015, 3:121-133. (Year: 2015).*
International Search Report for PCT/KR2016/009377 (PCT/ISA/210) dated Dec. 5, 2016.
Frampton et al., "Fabrication and optimization of alginate hydrogel constructs for use in 3D neural cell culture", Biomedical Materials, 2011, vol. 6, 18 pages.
Hahn et al., "Three-Dimensional Biochemical and Biomechanical Patterning of Hydrogels for Guiding Cell Behavior", Advanced Materials, 2006, vol. 18, pp. 2679-2684.
Hunt et al., "Calcium-Alginate Hydrogel-Encapsulated Fibroblasts Provide Sustained Release of Vascular Endothelial Growth Factor", Tissue Engineering: Part A, 2013, vol. 19, pp. 905-914.
Korean Patent Office communication for Korean Patent Application No. 10-2015-0118868, dated May 26, 2017.
Lee et al., "Bioinspired Tuning of Hydrogel Permeability-Rigidity Dependency for 3D Cell Culture", Scientific Reports, 2015, vol. 5, 7 pages.
Lee et al., "Diffusion-mediated in situ alginate encapsulation of cell spheroids using microscale concave well and nanoporous membrane", Lab Chip, 2011, vol. 11, pp. 1168-1173.
Lee et al., "In situ formation and collagen-alginate composite encapsulation of pancreatic islet spheroids", Biomaterials, 2012, vol. 33, pp. 837-845.
Office Action for Korean Patent Application No. 10-2015-0118868, dated Feb. 28, 2017.
Wang et al., "Engineering interconnected 3D vascular networks in hydrogels using molded sodium alginate lattice as the sacrificial template", Lab Chip, 2014, vol. 14, pp. 2709-2716.
Written Opinion of the International Searching Authority for PCT/KR2016/009377 (PCT/ISA/237) dated Dec. 5, 2016.

* cited by examiner

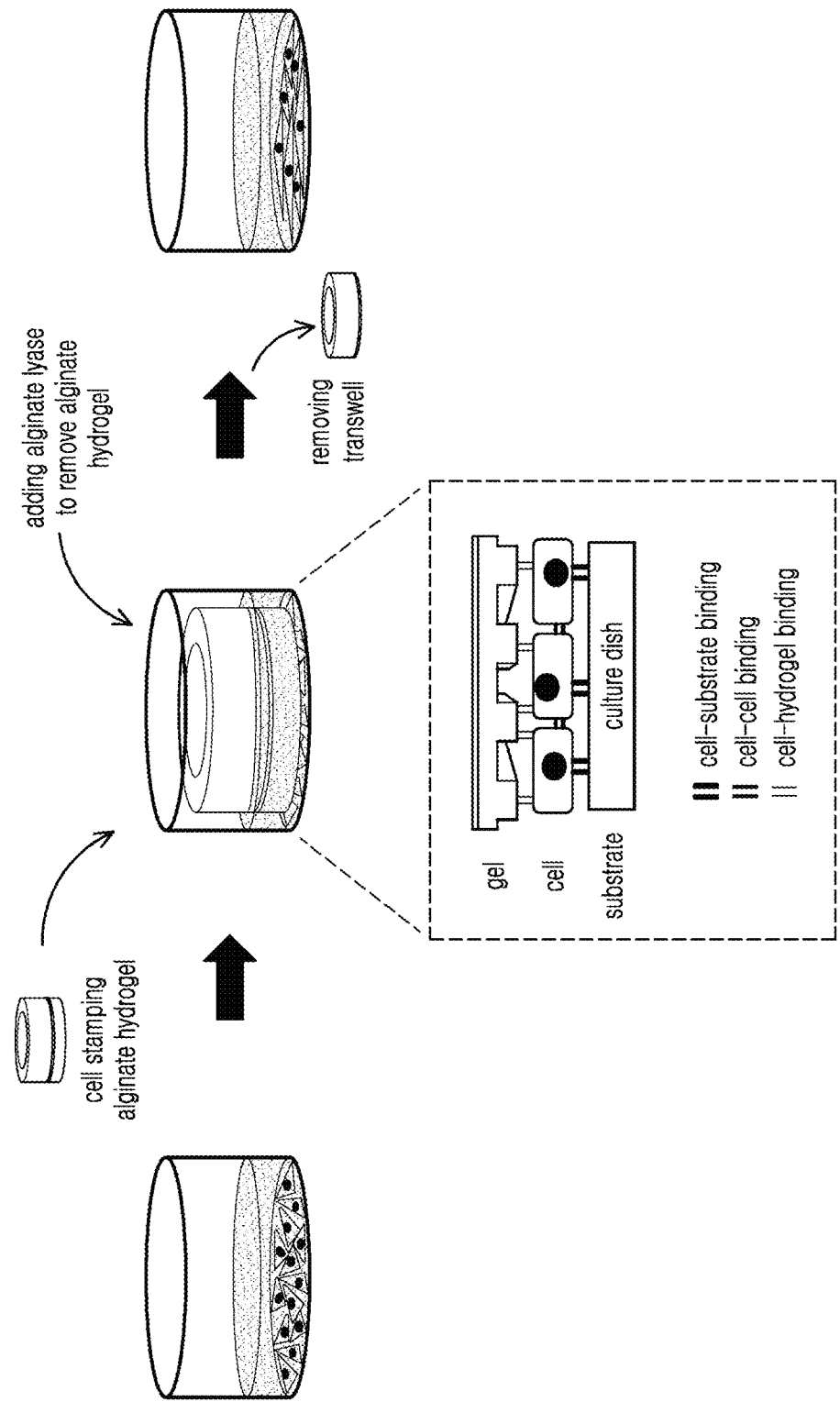

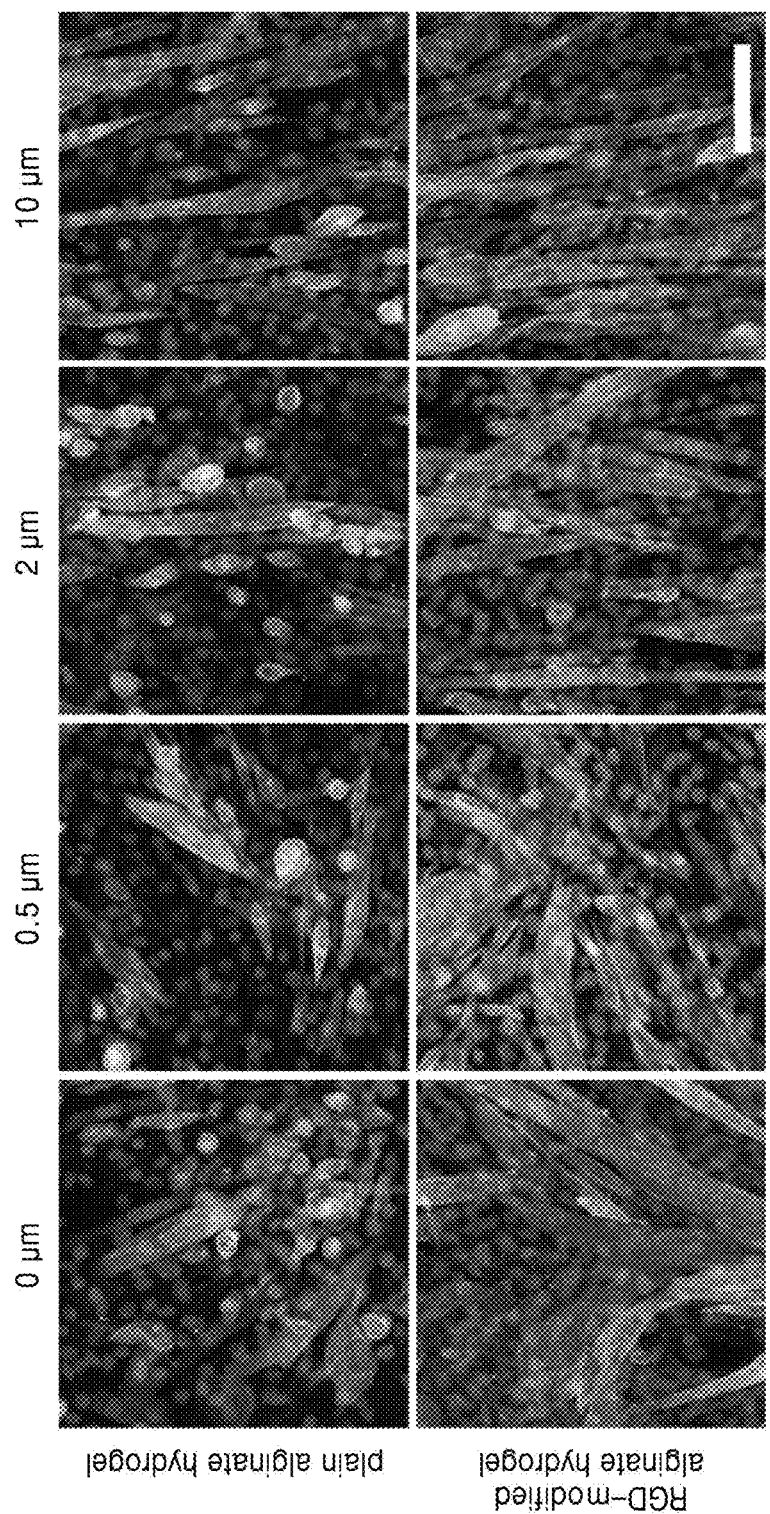

CELL PATTERNING MATERIAL, PREPARATION METHOD THEREOF, AND USE THEREOF

CROSS REFERENCE TO RELATED APPLICATIONS

This application is the National Phase of PCT International Application No. PCT/KR2016/009377, filed on Aug. 24, 2016, which claims priority under 35 U.S.C. 119(a) to Patent Application No. 10-2015-0118868, filed in Republic of Korea on Aug. 24, 2015, all of which are hereby expressly incorporated by reference into the present application.

TECHNICAL FIELD

The present disclosure relates to a cell patterning material, a method of preparing the cell patterning material, and a use of the cell patterning material.

BACKGROUND ART

Cell patterning technologies of selectively immobilizing cells in a specific region at the micrometer scale provide a model system for studying cell biology such as cell-to-cell, cell-to-surface, or cell-to-matrix interactions, and are base technologies for the development of biosensors and biochips. Recently, along with the need for high-throughput screening being emphasized in order to reduce the costs of in-vitro assay, diagnosis, and development of new drugs and achieve high efficiency, efforts to manufacture an array of cells and reduce the size of such cell arrays using cell patterning technologies are ongoing.

Recently, as a cell patterning method, a microcontact printing method has been widely used, the method involving micropatterning a two-dimensional surface such as metal or plastic using photolithography or soft lithography and culturing cells on the patterned surface while controlling incubation conditions and growth of the cells.

However, in the culturing of cells on such a micropatterned substrate, cell culture conditions may be modified and there are difficulties in controlling strength or conditions of physical stimulation caused by cell patterning.

Therefore, there are needs for a cell patterning method that may control stimulation caused by cell patterning while maintaining cell incubation conditions, and a microsensor using the cell patterning method.

DETAILED DESCRIPTION OF THE INVENTION

Technical Problem

The present invention provides a cell patterning material.

The present invention provides a method of preparing the cell patterning material.

The present invention provides a cell patterning method using the cell patterning material.

The present invention provides a biosensor including patterned cells.

Technical Solution

According to an aspect of the present invention, a cell patterning material includes a biocompatible polymer hydrogel adhered to a lower portion of a chamber comprising a microporous membrane at the lower portion.

The chamber including a microporous membrane at the lower portion may be referred to as a transwell chamber, a transwell upper chamber, or a transwell insert. The microporous membrane may be a support permeable to, for example, a buffer solution, a cellular material, or a culture medium, but impermeable to cells. A pore size of the microporous membrane may be appropriately chosen by one of ordinary skill in the art, for example, may be about 0.4 µm to about 0.8 µm. For example, the microporous membrane may include polycarbonate, polyester, or collagen-coated polytetrafluoroethylene. The microporous membrane may be adhered to the lower portion of the chamber, forming a bottom surface of the chamber. The chamber, any one widely used in the art, may be a commercially available product.

As used herein, the term "biocompatible" may refer to characteristics of material substantially not causing a harmful reaction when introduced into the body. For example, it means that an external thing or material, when introduced into the body, does not induce a harmful reaction such as inflammatory and/or immune responses. A biocompatible material may include a biodegradable material and a biostable material.

The biocompatible polymer may be a material including a natural or synthetic polymer. The biocompatible polymer may be a polymeric material that may be changed into a lower-molecular weight compound during a degradation process such as through metabolism of an organism, hydrolysis, enzymatic actions, or a combination of these processes. For example, the biocompatible polymer may include alginate, collagen, gelatin, elastin, silk, starch, chitosan, polylactide (PLA), polyglycolide (PGA), poly(lactic-co-glycolic acid) (PLGA), polyorthoester, polyanhydride, polyamino acid, polyhydroxybutyric acid, polycaprolactone, polyalkylcarbonate, polytrimethylene carbonace (PTMC), a copolymer of the forgoing polymers, ethyl cellulose, guar gum, or a combination of the forgoing polymers.

The biocompatible polymer hydrogel may be in a pattern. In the pattern of the biocompatible polymer hydrogel including a groove and ridge, the groove may have, for example, a width of about 0.1 µm to about 50 µm, about 1 µm to about 50 µm, about 1 µm to about 40 µm, about 1 µm to about 30 µm, about 1 µm to about 20 µm, about 1 µm to about 10 µm, or about 10 µm, and the ridge may have, for example, a width of about 0.1 µm to about 50 µm, about 1 µm to about 50 µm, about 1 µm to about 40 µm, about 1 µm to about 30 µm, about 1 µm to about 20 µm, about 1 µm to about 10 µm, or about 10 µm. A height between the groove and the ridge in the pattern of the biocompatible polymer hydrogel may be, for example, about 0.1 µm to about 50 µm, about 0.1 µm to about 40 µm, about 0.1 µm to about 30 µm, about 0.1 µm to about 20 µm, about 0.1 µm to about 10 µm, about 0.1 µm to about 5 µm, about 0.1 µm to about 2 µm, about 0.1 µm to about 1 µm, or about 0.1 µm to about 0.5 µm. A pattern length of the biocompatible polymer hydrogel may vary according to a size or shape of the chamber. For example, the biocompatible polymer hydrogel may have a pattern length of about 0.1 cm to about 50 cm, about 0.2 cm to about 40 cm, about 0.3 cm to about 30 cm, about 0.4 cm to about 20 cm, about 0.5 cm to about 15 cm, about 0.5 cm to about 10 cm, or about 1 cm to about 5 cm.

The biocompatible polymer hydrogel may be an alginate hydrogel. The alginate of the alginate hydrogel may or may not include a polypeptide having an amino acid sequence of arginine-glycine-aspartic acid (Arg-Gly-Asp: RGD) at the N-terminus. The RGD amino acid sequence may be a binder or a ligand which mediates binding of alginate and cells.

The biocompatible polymer hydrogel may be adhered to the lower portion of the chamber including the microporous membrane. For example, the biocompatible polymer hydrogel may be adhered to the outside or a lower surface of the microporous membrane. The biocompatible polymer hydrogel may have a form of a membrane.

Cell patterning refers to reversibly fixing or aligning a plurality of cells in a specific location or direction at the micrometer scale. The cells may be living cells. Through cell patterning, cells may be stimulated to change its morphology, growth rate, or differentiation pathway.

According to an aspect of the present invention, a method of preparing a cell patterning material according to any of the embodiments includes: adding a biocompatible polymer solution onto a polymer mold having a pattern; contacting the biocompatible polymer solution on the polymer mold with the chamber including the microporous membrane at the lower portion thereof; adding a calcium solution into the chamber to gelate the biocompatible polymer solution into a biocompatible polymer hydrogel; and separating the biocompatible polymer hydrogel adhered to the chamber and the polymer mold from one another.

The chamber including a microporous membrane at its lower portion, the biocompatible polymer, and the biocompatible polymer hydrogel may be the same as described above.

The method of preparing the cell patterning material may include placing a biocompatible polymer solution onto a polymer mold having a pattern.

The polymer mold having a pattern may be manufactured using a method known in the art. In the pattern of the biocompatible polymer hydrogel including a groove and ridge, the groove may have, for example, about 0.1 µm to about 50 µm, about 1 µm to about 50 µm, about 1 µm to about 40 µm, about 1 µm to about 30 µm, about 1 µm to about 20 µm, about 1 µm to about 10 µm, or about 10 µm, and the ridge may have a width of about 0.1 µm to about 50 µm, about 1 µm to about 50 µm, about 1 µm to about 40 µm, about 1 µm to about 30 µm, about 1 µm to about 20 µm, about 1 µm to about 10 µm, or about 10 µm. A height between the groove and the ridge in the pattern of the biocompatible polymer hydrogel may be, for example, about 0.1 µm to about 50 µm, about 0.1 µm to about 40 µm, about 0.1 µm to about 30 µm, about 0.1 µm to about 20 µm, about 0.1 µm to about 10 µm, about 0.1 µm to about 5 µm, about 0.1 µm to about 2 µm, about 0.1 µm to about 1 µm, or about 0.1 µm to about 0.5 µm.

The polymer mold may include alkylsiloxane, polystyrene, polyacrylamide, polylactic acid, polyhydroxy acid, polyamide, polyamino acid, polyacetal, polycyanoacrylate, polyurethane, polypyrrole, polyester, polymethacrylate, polyethylene, polycarbonate, polyepoxyethane, or a combination thereof. For example, the alkylsiloxanemay be polydimethylsiloxane (PDMS).

A biocompatible polymer solution in a sol state may be placed onto the polymer mold having a pattern. For example, the biocompatible polymer solution in a sol state may be dropped onto the polymer mold having a pattern. The biocompatible polymer solution may be an alginate solution. The alginate solution may be an alginate solution including or excluding a RGD amino acid sequence.

The method of preparing the cell patterning material may include contacting the biocompatible polymer solution on the polymer mold with the chamber including a microporous membrane at its lower portion. For example, the chamber may be put on the biocompatible polymer solution on the polymer mold.

The method may include adding a calcium solution into the chamber including the microporous membrane at its lower portion to gelate the biocompatible polymer solution into a biocompatible polymer hydrogel. For example, as a calcium solution is added into the chamber, the calcium solution may pass through the microporous membrane of the chamber and gelate the biocompatible polymer solution. Since the biocompatible polymer solution is on the polymer mold having a pattern, a biocompatible polymer hydrogel having a pattern of an opposite form to the pattern of the polymer mold may be obtained as the biocompatible polymer solution is gelated.

The calcium solution may be a $CaCl_2$ solution, a $CaSO_4$ solution, or a $CaCO_3$ solution.

The method may include separating the biocompatible polymer hydrogel adhered to the chamber, and the polymer mold from one another. For example, the biocompatible polymer hydrogel adhered to the chamber may be separated from the polymer mold.

According to an aspect of the present invention, a cell patterning method includes: contacting cells and the cell patterning material according to any of the above-described embodiments to obtain patterned cells; adding a biocompatible polymer lyase or a calcium-chelating agent to the chamber of the cell patterning material to remove the biocompatible polymer hydrogel; and separating the patterned cells and the chamber from one another.

The chamber including a microporous membrane at its lower portion, the biocompatible polymer, the biocompatible polymer hydrogel, and the cell patterning material may be the same as described above.

The cell patterning method may include contacting cells and a cell patterning material according to any of the embodiments including a biocompatible polymer hydrogel adhered to a lower portion of a chamber including a microporous membrane at the lower portion.

The cells may be muscle cells, nerve cells, stem cells, connective tissue cells, vascular cells, or epithelial cells.

The contacting of the cells and the cell patterning material may be covering an upper portion of the cell adhered to a culture dish with the chamber including the microporous membrane at the lower portion thereof, such that the lower portion of the chamber contacts the upper portion of the cell. For example, the contacting of the cells and the cell patterning material may be contacting the upper portion of the cell adhered to a culture dish with bottom surface of the porous membrane of the chamber.

The contacting time of the cells and the cell patterning material may be, for example, about 1 min to about 24 hours, about 1 min to about 18 hours, about 1 min to about 12 hours, about 1 min to about 6 hours, about 1 min to about 1 hour, about 1 min to about 30 mins, or about 1 min to about 5 mins. By contacting the cells and the cell patterning material, the biocompatible polymer hydrogel may apply a physical stimulus to the cells. The cells may be patterned according to the pattern of the biocompatible polymer hydrogel of the cell patterning material.

The cell patterning method may include adding a biocompatible polymer lyase or a calcium-chelating agent to the chamber of the cell patterning material to remove the biocompatible polymer hydrogel. For example, the biocompatible polymer hydrogel may be removed by adding a biocompatible polymer lyase or a calcium-chelating agent to the inside or outside of the chamber of the cell patterning material. The biocompatible polymer lyase may be alginate lyase. The biocompatible polymer lyase may break down the biocompatible polymer hydrogel adhered to the lower portion of the chamber. The calcium-chelating agent may change the biocompatible polymer hydrogel adhered to the lower portion of the chamber back into the biocompatible polymer solution in a sol state. The calcium-chelating agent may be citrate, ethylenediamine tetraacetic acid (EDTA), ethyleneglycol tetraacetic acid (EGTA), 1,2-Bis(2-aminophenoxy)ethane-N,N,N',N'-tetraacetic acid tetrakis(acetoxymethyl ester) (BAPTA-AM), or a combination thereof.

The cell patterning method may further include an incubation step after the adding of a biocompatible polymer lyase or a calcium-chelating agent to the chamber of the cell patterning material. The incubation time may be, for example, about 1 min to about 48 hours, about 1 min to about 36 hours, about 1 min to about 24 hours, about 1 min to about 12 hours, about 1 min to about 6 hours, or about 1 min to about 1 hour. After a certain level of stimulation is applied to the cells for a certain time by the biocompatible polymer hydrogel, the biocompatible polymer hydrogel may be removed by using a biocompatible polymer lyase or a calcium-chelating agent. The strength of physical stimulus in cell patterning or cell patterning conditions may be controlled.

The cell patterning method may include separating the patterned cells and the chamber from one another. For example, the chamber may be removed from a culture solution containing the patterned cells. The cell pattern of the obtained cells may be maintained for about 1 min to about 15 days, about 1 min to about 10 days, about 1 min to about 7 days, about 1 min to about 3 days, or about 1 min to about 1 day. Since the cell pattern of the cells may be maintained under the same cell culture environment even after the cell patterning material has been removed, it may be convenient to manufacture a cell array, a biochip, or a biosensor under the cell culture environment by using the cell patterning method.

The cell patterning method may further include changing a patterning direction of the patterned cells by contacting the patterned cells with the cell patterning material in a direction different from a previous contacting direction. The changing of the patterning direction to a different direction may be referred to as reversible patterning or reversible stamping.

According to an aspect of the present invention, a biosensor includes a cell pattern obtained by using the cell patterning method according to any of the above-described embodiments.

A biosensor refers to a device used to assay characteristics of material or cells based on functions of a living organism. The biosensor may be a device including a cell having a pattern formed by using the above-described method and a culture container to which the cell is adhered.

Advantageous Effects of the Invention

In a cell patterning material, a method of preparing the cell patterning material, a cell patterning method using the cell patterning material, and a biosensor including a cell pattern obtained by using the cell patterning method, according to the one or more embodiments, cells may be conveniently and efficiently patterned and the time for applying an external stimulus for patterning may be controlled. In addition, patterned cells may have an excellent proliferation rate and excellent differentiation efficiency, and may be re-patterned in a different direction, and high-throughput screening using the patterned cells is possible.

DESCRIPTION OF THE DRAWINGS

FIG. 2A is a schematic view for explaining a method of cell patterning through alginate hydrogel stamping, according to an embodiment.

FIG. 4A shows microscope images of stamped cells on the alginate hydrogels after immunostaining using anti-paxillin antibody and anti-MF20 antibody.

MODE OF THE INVENTION

One or more embodiments of the present disclosure will now be described in detail with reference to the following examples. However, these examples are only for illustrative purposes and are not intended to limit the scope of the one or more embodiments of the present disclosure.

Example 1. Cell Pattering Through Hydrogel Stamping

1. Preparation of Hydrogel Plate Having a Pattern Thereon

A polydimethylsiloxane (PDMS) mold (Sylgard 184 elastomer kit, available from Dowcorning) having an anisotropic pattern was prepared using soft lithography technology. The PMDS mold had a groove width of about 10 μm a ridge width of about 10 μm, and a height between the groove and the ridge of about 0 μm (flat), 0.5 μm, 2 μm, or 10 μm.

A 2% (w/v) RGD-modified alginate solution (PRONOVA™ UP MVG, Cat. No. 4200106) was added onto the PDMS mold, and then a transwell (Millipore® Millicell®cell culture plate inserts, a pore size of about 0.4 μm, a diameter of about 30 mm, Sigma-Aldrich, Cat. No. Z353086) was placed onto the alginate solution on the PDMS mold. About 1 mM of a $CaCl_2$ solution (available from Sigma-Aldrich) was added into the transwell to gelate the alginate. Then, the PDMS mold was removed, thereby preparing an alginate hydrogel (hereinafter, referred to as 'RGD-modified alginate hydrogel' or 'RGD-modified hydrogel') having a pattern adhered to the transwell. For comparison, an alginate hydrogel (hereinafter, referred to as 'plain alginate hydrogel' or 'plain hydrogel') having a pattern produced using RGD-free sodium alginate was prepared.

Figure 1A:
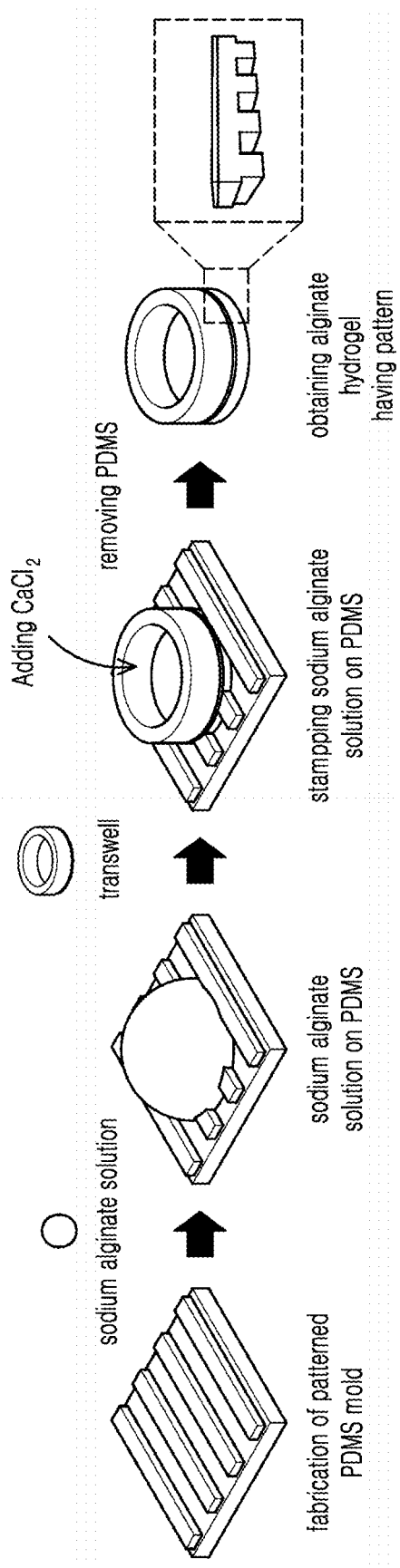
FIG. 1A is a schematic view for explaining a method of preparing an alginate hydrogel having a pattern.
Figure 1B:
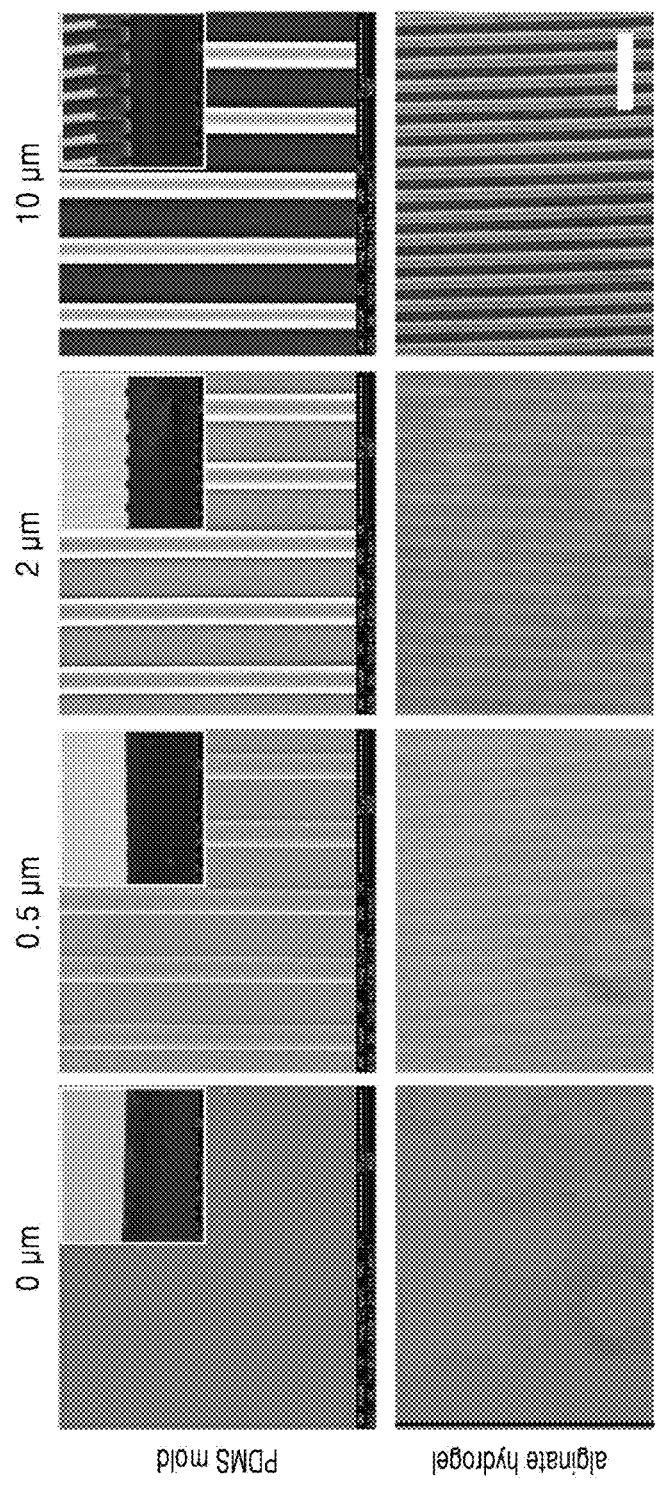
FIG. 1B shows electron microscope images of a polydimethylsiloxane (PDMS) mold and the alginate hydrogel.

FIG. 1A is a schematic view for explaining a method of preparing an alginate hydrogel having a pattern, wherein an enlarged image of the alginate hydrogel is indicated by a dashed rectangle. Electron microscope images of the PDMS mold and the alginate hydrogel are shown in FIG. 1B (White bar length: 50 µm). Referring to FIG. 1B, the prepared alginate hydrogel was found to have a pattern.

2. Verification of Cell Patterning Through Alginate Hydrogel Stamping (1) Morphology of Cells After a culture dish was inoculated with C2C12 mouse muscle myoblasts (ATCC, Cat. No. CRL-1772), a DMEM medium including 10% (v/v) fetal bovine serum (FBS) and 1% (w/v) penicillin-streptomycin (Gibco®, Life Technologies) was added into the culture dish inoculated with the cells, and the inoculated cells were cultured at 37° C. under 5% $CO_2$ conditions for about 24 hours.

The above-prepared alginate hydrogel as described in Section 1 were placed onto the cells in the culture dish, and the cells were incubated at about 37° C. under 5% $CO_2$ conditions for about 12 hours to about 24 hours. A plain alginate hydrogel was used as a negative control group.

As the layer of the cells was placed on the culture dish and the alginate hydrogel having a pattern was placed thereon, the alginate hydrogel physically stimulated the layer of the cells in the culture dish, thereby causing the layer of the cells to have a pattern corresponding to the pattern of the alginate hydrogel. Next, 4 units/ml of an alginate lyase (Sigma, a1603) was added into the culture dish, which was then incubated at about 37° C. for about 60 minutes or more to break down the alginate hydrogel, and then the transwell was removed from the culture dish.

This method of cell patterning through alginate hydrogel stamping is schematically illustrated in FIG. 2A, together with binding states of cells in a dashed rectangle.

Figure 2B:
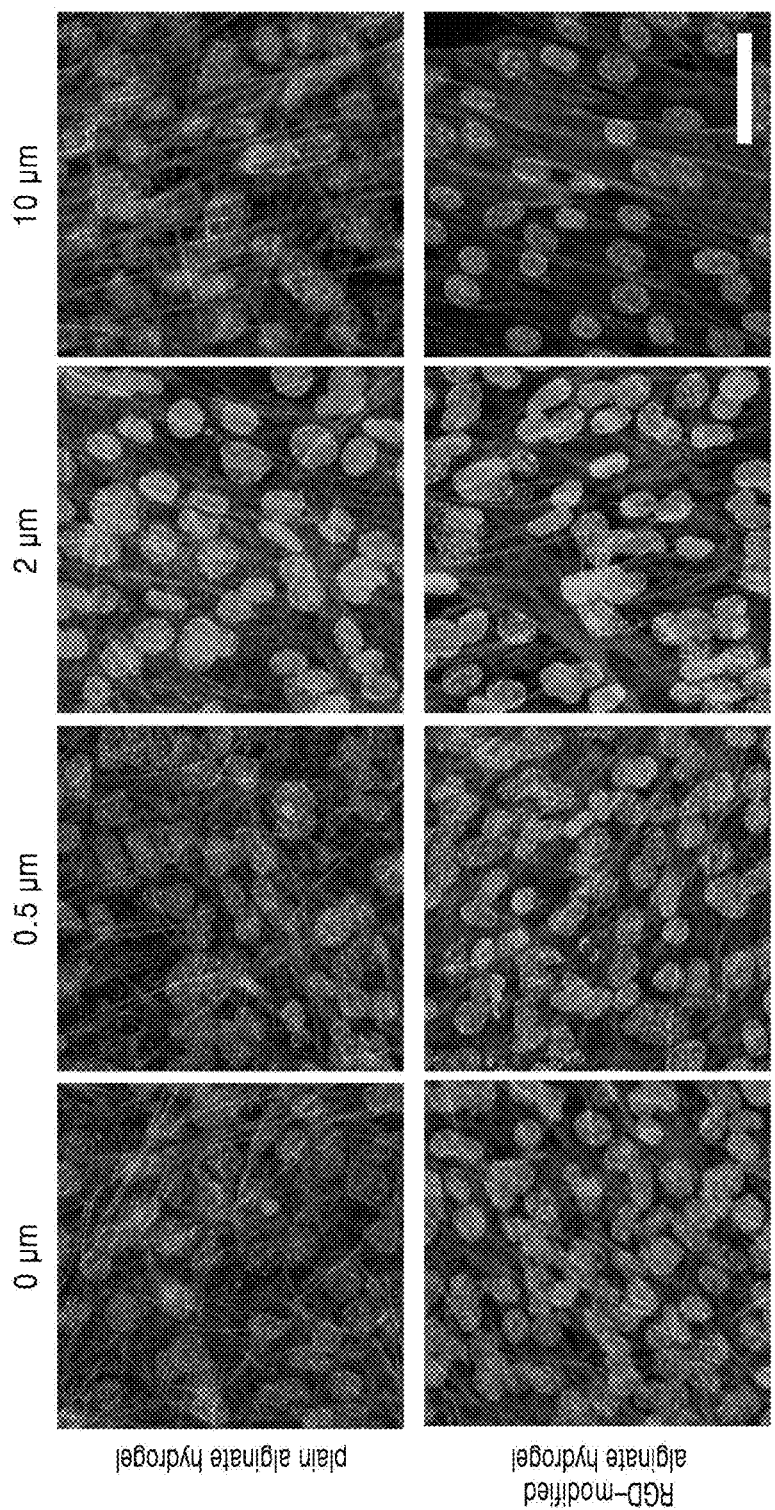
FIG. 2B shows microscope images of stamped cells.

After the alginate hydrogel stamping, the cells were fixed with paraformalin, and the cytoskeleton was stained with rhodamine-phalloidin. The stained cells were observed using a fluorescent microscope. The resulting microscope images are shown in FIG. 2B (White bar length: 50 µm). The cells stamped with the plain alginate hydrogel of zero height (0 µm) or the RGD-modified alginate hydrogel of zero height (0 µm) had nearly no orientation. As the heights of the plain alginate hydrogel and the RGD-modified alginate hydrogel with which the cells were stamped were increased, the cells had improved orientation. Accordingly, it was found that cell patterning using the alginate hydrogel having a pattern is possible.

(2) Morphology of Cells and Nuclei

As described above in Section 2(1), while the alginate hydrogel having a pattern (a height between the groove and the ridge of about 0 µm (flat), 0.5 µm, 2 µm, or 10 µm) was placed on the C2C12 cells, cell incubation was performed at about 37° C. under 5% $CO_2$ conditions for about 24 hours. RGD-free plain alginate hydrogel was used as a control group.

Figure 2C:
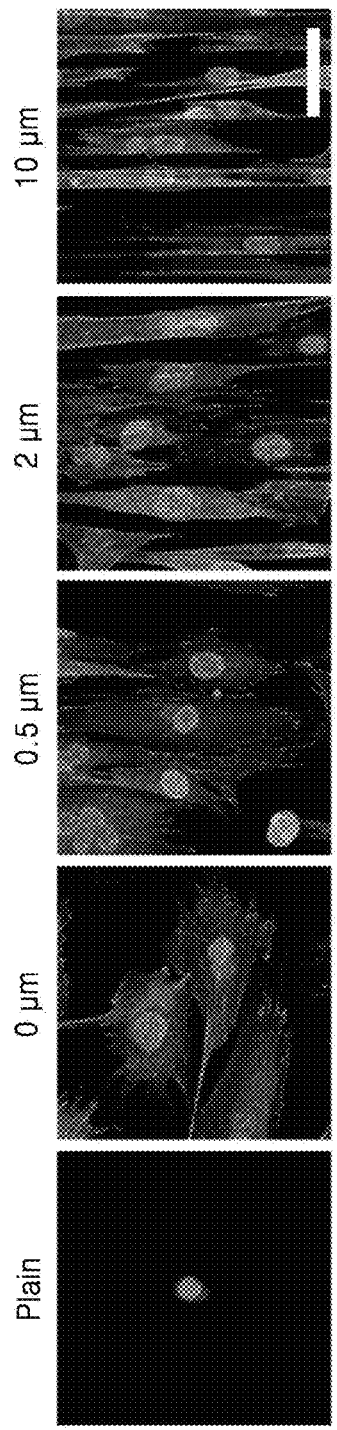
FIG. 2C shows microscope images of stamped cells after focal adhesion and staining filamentous actin (F-actin) and nuclei.

Then, the cells were fixed with paraformalin and stained with a FITC-labeled anti-vinculin antibody (available from SANTA CRUZ BIOTECHNOLOGY, USA), rhodamine-labeled filamentous actin (F-actin) reagent (available from Invitrogen, USA), and 4',6-diamidino-2-phenylindole (DAPI) (available from Invitrogen, USA). The stained cells were observed using a fluorescent microscope, and an aspect ratio of the nucleus (a ratio of the shorter axis length to the longer axis length) was calculated. The fluorescent microscope images of the cells are shown in FIG. 2C (White bar length: 50 µm). The results of calculating the aspect ratios of the nuclei are shown in FIG. 2D.

Figure 2D:
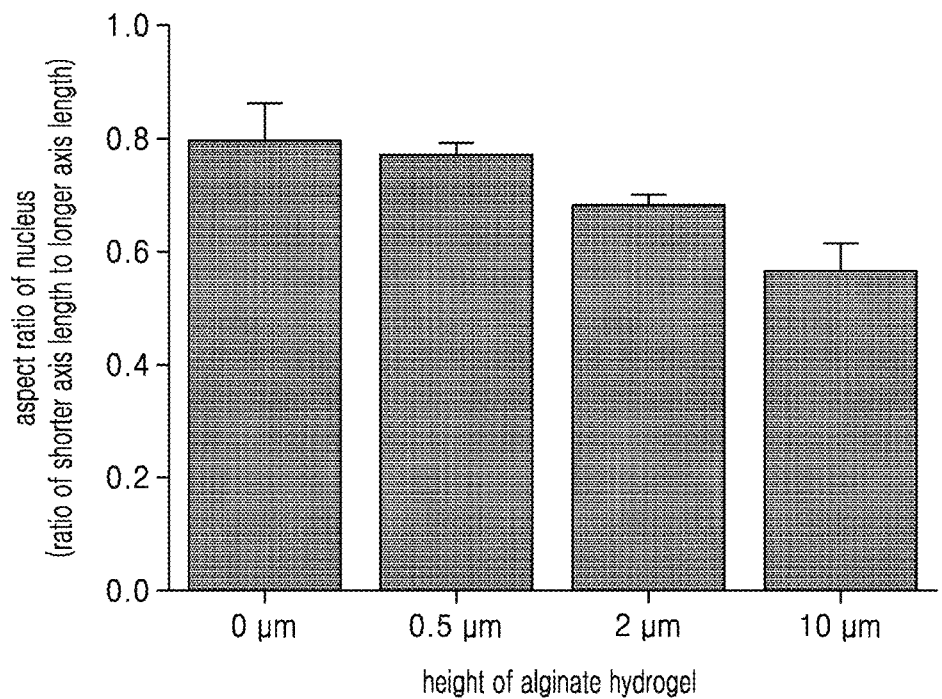
FIG. 2D is a graph illustrating aspect ratios of nuclei.

Referring to FIGS. 2C and 2D, it was found that with increasing heights between the groove and the ridge of the RGD-modified alginate hydrogels with which the cells were stamped, the stamped cells had increased orientation and a long nucleus shape due to reduced aspect ratio of the nucleus.

The shape of the nucleus was observed with a fluorescent microscope in real time throughout the stamping process (for about 24 hours). As a result, the morphology of the nucleus of the cells stamped with the RGD-modified alginate hydrogel (in particular, having a height of about 10 µm) was found to have rapidly changed, compared to that of the cells stamped with the plane alginate hydrogel.

(3) Change in Expression of Adhered Protein

Figure 2E:
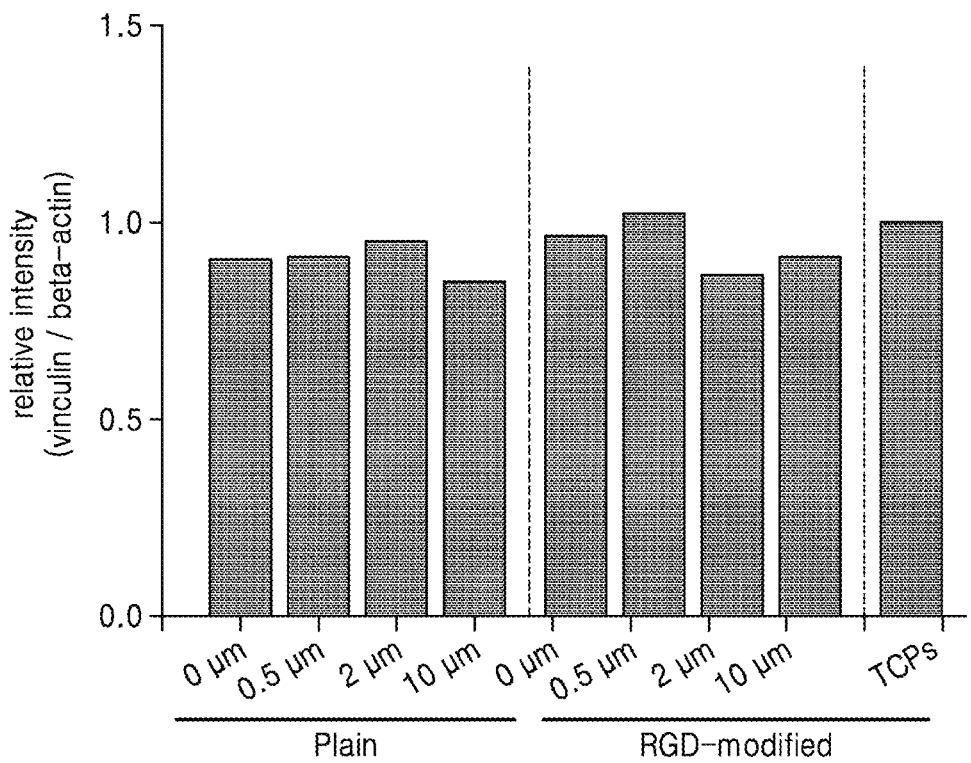
FIG. 2E is a graph of relative intensities of vinculin to beta-actin in total protein of the stamped cells.
Figure 2F:
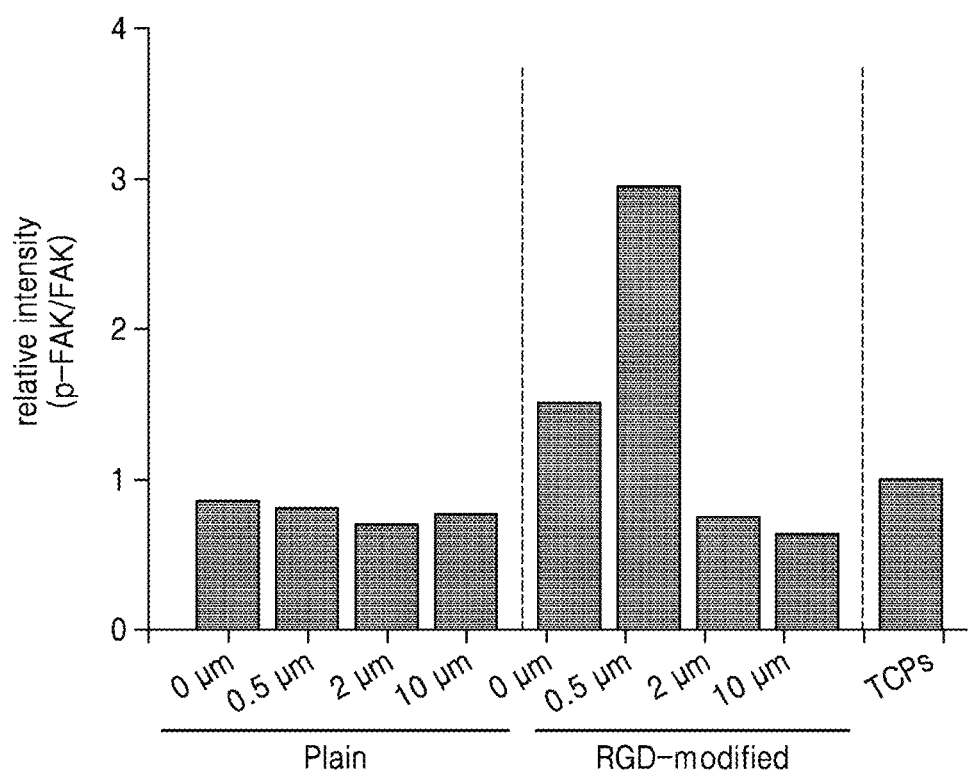
FIG. 2F is a graph of relative intensities of phosphorylated focal adhesion kinase (FAK) to FAK in the total protein of the stamped cells.

A total protein of the stamped cells was analyzed by electrophoresis, immunoblotting with anti-vinculin (Vinculin) antibody (SANTA CRUZ BIOTECHNOLOGY, USA), anti-focal adhesion kinase (FAK) antibody (Cell signaling, USA), anti-phospho FAK antibody (Cell signaling, USA), and anti-beta-actin antibody (Abclonal, China), and measuring relative intensities of the proteins using Image J software. The measured relative intensities of vinculin to beta-actin and those of phosphorylated FAK to FAK are shown in FIGS. 2E and 2F. Referring to FIGS. 2E and 2F, the expressed amounts of the adhered proteins were found to be different according to the types of the alginate hydrogel (Tissue culture polystyrene (TCPs, available from Corning, USA) used as cell culture dishes).

3. Determination of Characteristics of Cell Pattern Obtained By Alginate Hydrogel Stamping (1) Change of Cell Pattern According to Height and Stamping Time of Alginate Hydrogel After cell stamping using the plain alginate hydrogel or RGD-modified alginate hydrogel having a height of about 0 µm, about 0.5 µm, about 2 µm, or about 10 µm for about 0 min, 5 min, 30 min, or 60 min by using the method as described above in Section 2(1), 4 units/ml of alginate lyase (available from Sigma, a1603) was added to each culture dish, and the culture dishes were incubated at about 37° C. for about 120 minutes to break down the alginate hydrogel. After removing the transwells from the culture dishes, the cells in the culture dishes were stained with rhodamine-phalloidin (Invitrogen, R415). As negative control groups, cells stamped using a plain PDMS mold or a fibronectin (FN)-coated PDMS mold were used.

Figure 3A:
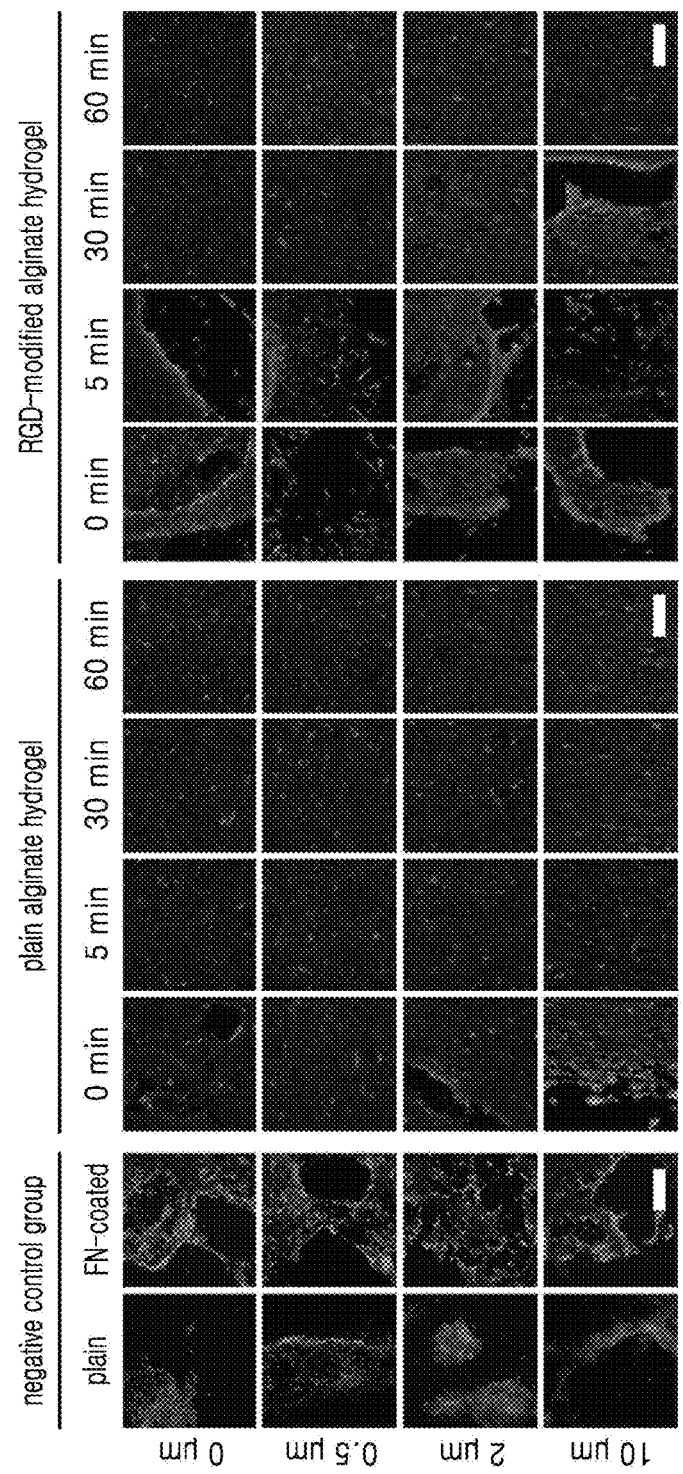
FIG. 3A shows microscope images of stamped cells with respect to height of alginate hydrogels and the stamping time, wherein a negative control group is cells on PDMS molds.

The stained cells were observed using a fluorescent microscope. The obtained fluorescent microscope images are shown in FIG. 3A (White bar length: 200 µm). Referring to FIG. 3A, as the height of the alginate hydrogel and the stamping time were increased, the cells became more aligned. Thus, it was found that in the cells stamped on the alginate hydrogel having a pattern, cell patterning may be controlled according to the height of the alginate hydrogel and the stamping time.

(2) Proliferation Rate of Cells Stamped Using Alginate Hydrogel

In order to verify proliferative capacity of the cells stamped on the plain alginate hydrogel or RGD-modified alginate hydrogel, the cells were subjected to 5-bromo-2'-deoxyuridine (BrdU) absorption staining.

Figure 3B:
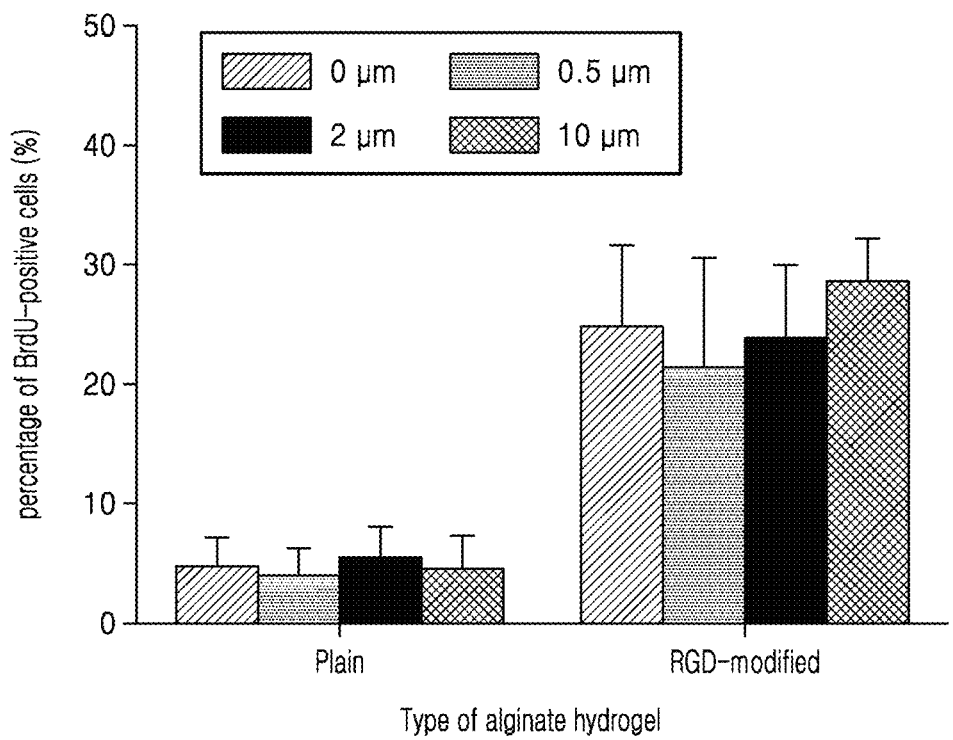
FIG. 3B is a graph of percentage (%) of BrdU-positive cells in the cells stamped on the alginate hydrogels for about 24 hours.

After cell stamping using the plain alginate hydrogel or RGD-modified alginate hydrogel having a height of about 0 μm, about 0.5 μm, about 2 μm, or about 10 μm for about 24 hours as described above in Section 2(1), 4 units/ml of alginate lyase (available from Sigma, a1603) was added to each culture dish, and the culture dishes were incubated at about 37° C. for about 60 minutes to break down the alginate hydrogel. After removing the transwells from the culture dishes, the cells in the culture dishes were stained with DAPI (Invitrogen, USA) and BrdU (Sigma, USA) according to manufacturer's instructions. Blue fluorescence was detected in the nuclei of the cells, while green fluorescence was detected in the nuclei of cells absorbing BrdU. A percentage of the number of the nuclei stained with BrdU with respect to total number of nuclei was calculated as a percentage of BrdU-positive cells (%). The results are shown in FIG. 3B. Referring to FIG. 3B, the cells stamped on the RGD-modified alginate hydrogel had a significantly higher proliferation rate than the cells stamped on the plain alginate hydrogel.

Figure 3C:
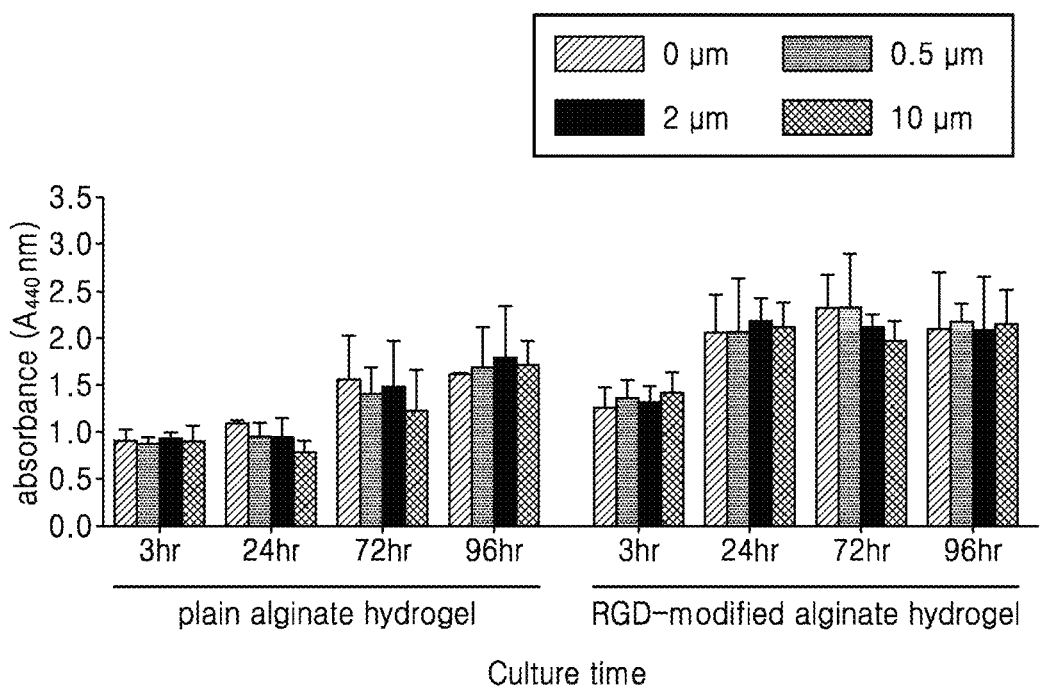
FIG. 3C is a graph of absorbance in a WST-1 assay illustrating proliferative capacity of the stamped cells.

After cell stamping for about 24 hours, incubation together with alginate lyase for about 60 minutes, and removing the alginate hydrogel, the cells were further cultured for about 96 hours. Proliferative capacities of the cultured cells were quantitatively measured using a WST-1 cell proliferation reagent (available from Daeil Lab, Korea). The results are shown in FIG. 3C. Referring to FIG. 3C, the cells stamped on the RGD-modified alginate hydrogel were found to more rapidly proliferate than the cells stamped on the plain alginate hydrogel.

Figure 3D:
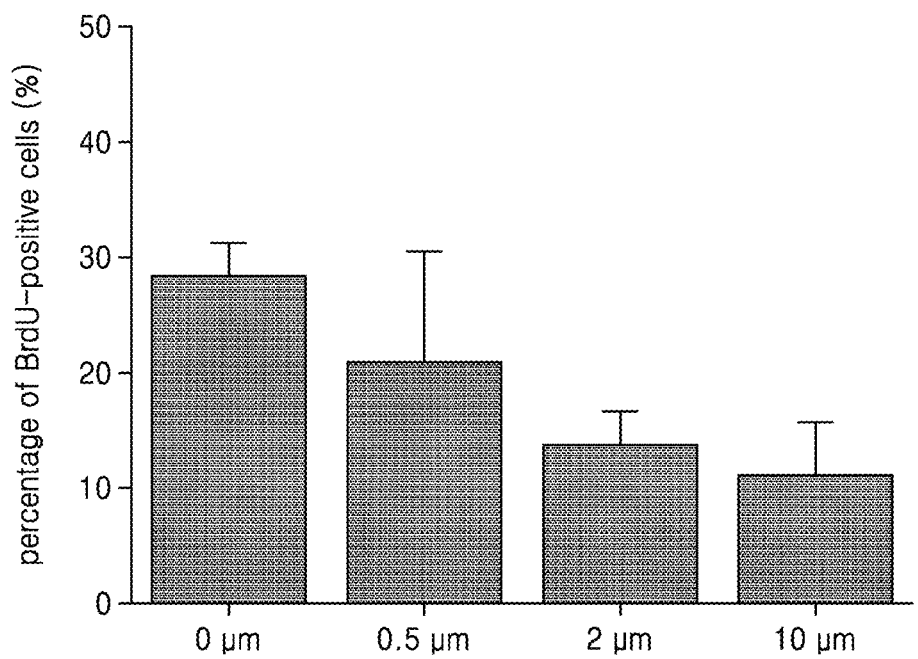
FIGS. 3D and 3E are graphs of percentage of the nuclei stained with BrdU and absorbance in a WST-1 assay, respectively, in cells cultured on fibronectin-coated PDMS molds.
Figure 3E:
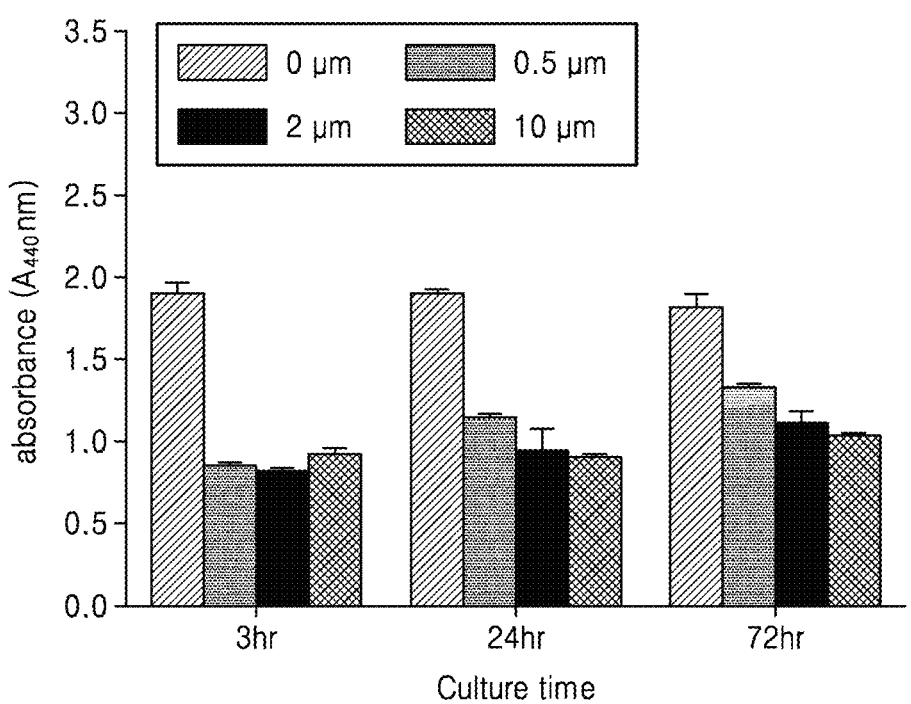

As a comparative example, the cells on the FN-coated PDMS molds were cultured, and a percentage of the number of nuclei stained with BrdU (BrdU-positive cells) in each mold, and absorbance in WST-1 cell proliferation assay in the stamped cells were obtained. The results are shown in FIGS. 3D and 3E. Referring to FIGS. 3D and 3E, it was found that the cells cultured on the FN-coated PDMS molds had a reduced cell proliferation rate as the height between the groove and the ridge increased.

Accordingly, the cells stamped on the RGD-modified alginate hydrogel were found to more rapidly proliferate in a short time with a higher proliferation rate, compared to the cells cultured on the plain alginate hydrogel or the cells cultured on the FN-coated PDMS molds.

(3) Differentiation Characteristics of Cells Stamped on Alginate Hydrogel

After cell stamping using the plain alginate hydrogel or RGD-modified alginate hydrogel having a height of about 0 μm, about 0.5 μm, about 2 μm, or about 10 μm for about 12 hours to about 24 hours by using the method as described above in 2(1), 4 units/ml of alginate lyase (available from Sigma, a1603) was added to each culture dish, and the culture dishes were incubated at about 37° C. for about 120 minutes to break down the alginate hydrogel. After removing the transwells from the culture dishes, the cells were fixed using paraformaldehyde.

Figure 4B:
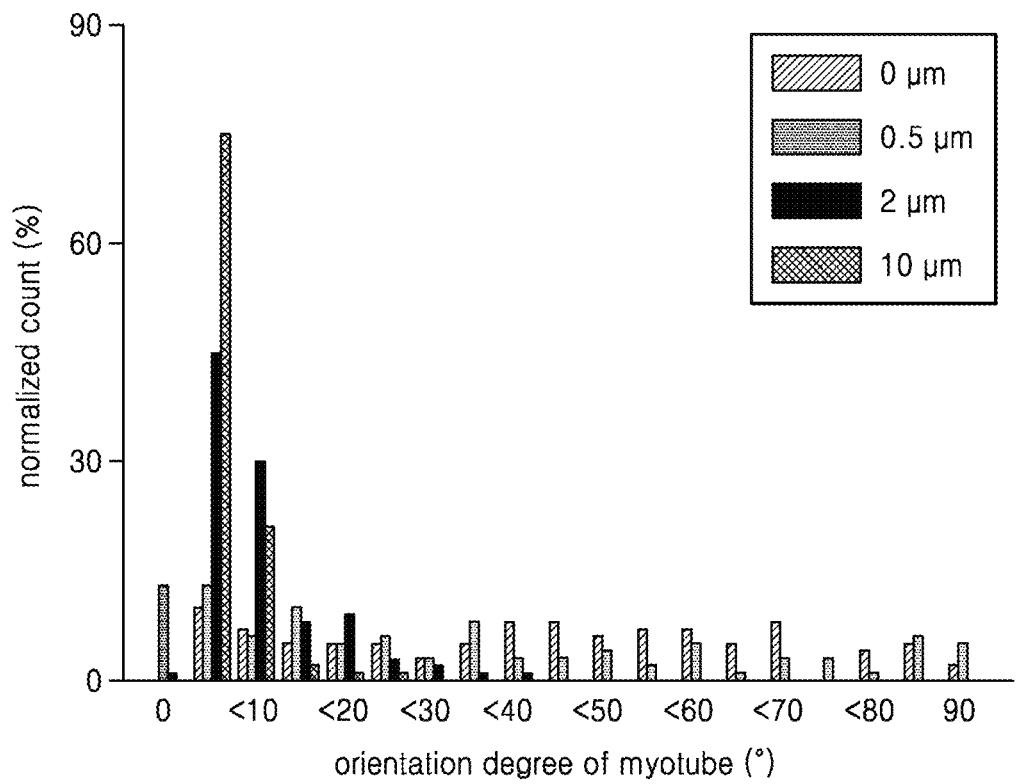
FIGS. 4B and 4C are graphs showing the orientation of myotubes in cells stamped on the plain alginate hydrogel and the RGD-modified alginate hydrogel, respectively.
Figure 4C:
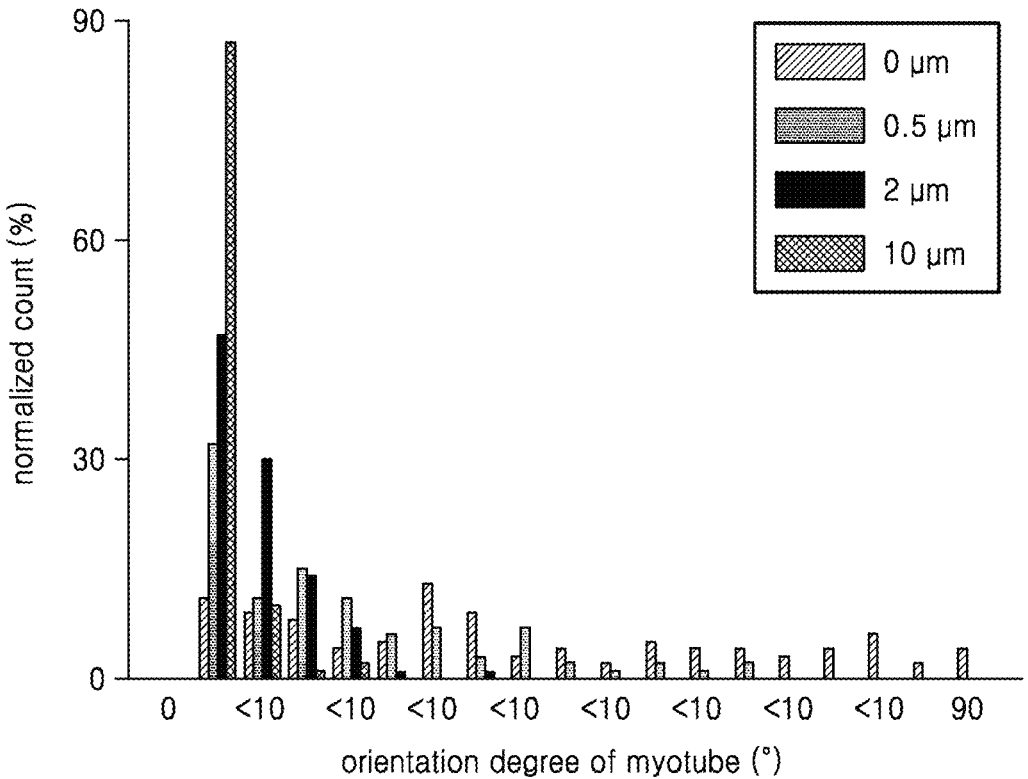
Figure 4D:
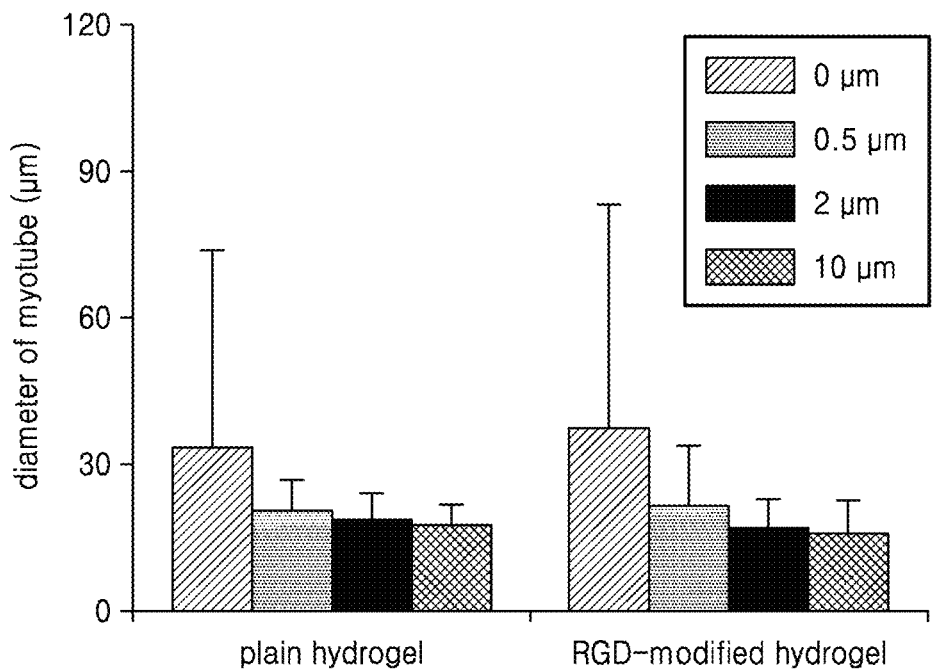
FIGS. 4D and 4E are graphs of diameter of myotubes and percentage of nuclei within myotubes, respectively, in the cells stamped on the plain alginate hydrogel or the RGD-modified alginate hydrogel.
Figure 4E:
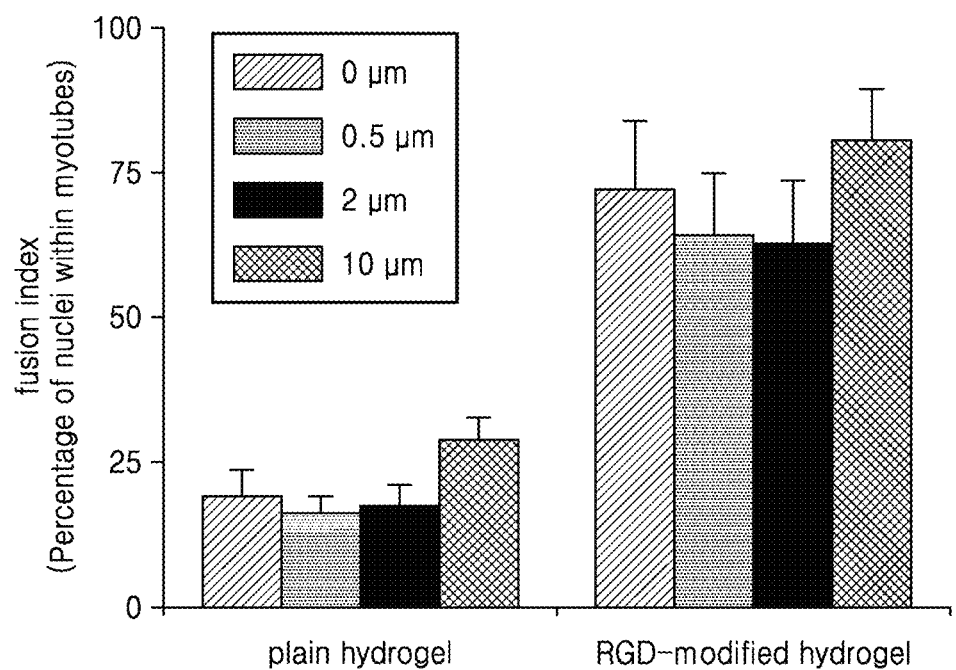

In order to detect F-actin and MF20 known as myotube markers of muscle cell differentiation that appear in the cytoskeleton, the fixed cells were immunostained by adding rhodamine-phalloidin (Invitrogen, R415) and anti-MF20 antibody (MF20, Developmental Studies Hybridoma Bank, USA) thereto. After the immunostaining, the cells were observed using a fluorescent microscope. The microscope images of the cells immunostained with an anti-paxillin antibody and an anti-MF20 antibody are shown in FIG. 4A (White bar length: 100 μm). Orientation of the myotubes stained with the anti-MF20 antibody was analyzed. The orientations of the myotubes in the cells stamped on the plain alginate hydrogel and the RGD-modified alginate hydrogel are shown in FIGS. 4B and 4C, respectively. The diameter of myotubes and the percentage of nuclei within myotubes are shown in FIGS. 4D and 4E, respectively. The percentage of nuclei within myotubes (%) was calculated as a ratio of the number of nuclei in myotubes to total number of nuclei within myotubes), indicating the fusion index of muscle cells.

Referring to FIGS. 4A to 4C, it was found that the cells stamped on the RGD-modified alginate hydrogel and the myotubes in the cells were better oriented than the cells stamped on the plain alginate hydrogel. The cells stamped on the RGD-modified alginate hydrogel and muscle fibers appearing in muscle differentiation were found to be well aligned along the pattern direction according to the heights of the alginate hydrogel. Referring to FIGS. 4D and 4E, the cells stamped on the RGD-modified alginate hydrogel were found to have a larger diameter of myotubes and a larger fusion index, compared to the cells stamped on the plane alginate hydrogel. Accordingly, it was found that the cells stamped on the RGD-modified alginate hydrogel could significantly differentiate into muscle cells.

(3) Maintenance of Cell Pattern After Removing Alginate Hydrogel

It was evaluated whether a cell pattern of the cells stamped on the alginate hydrogel having a pattern was maintained or not after the alginate hydrogel had been removed.

After cell stamping using the plain alginate hydrogel or RGD-modified alginate hydrogel having a height of about 0 μm, about 0.5 μm about 2 μm, or about 10 μm for about 12 hours to 24 hours by using the method as described above in Section 2(1), the alginate hydrogel was broken down using alginate lyase. After removing the transwells from the culture dishes, the stamped cells in the culture dishes were incubated at about 37° C. under 5% $CO_2$ conditions for 0 days, 3 days, or 7 days. Then, the incubated cells were fixed using paraformaldehyde.

Figure 5:
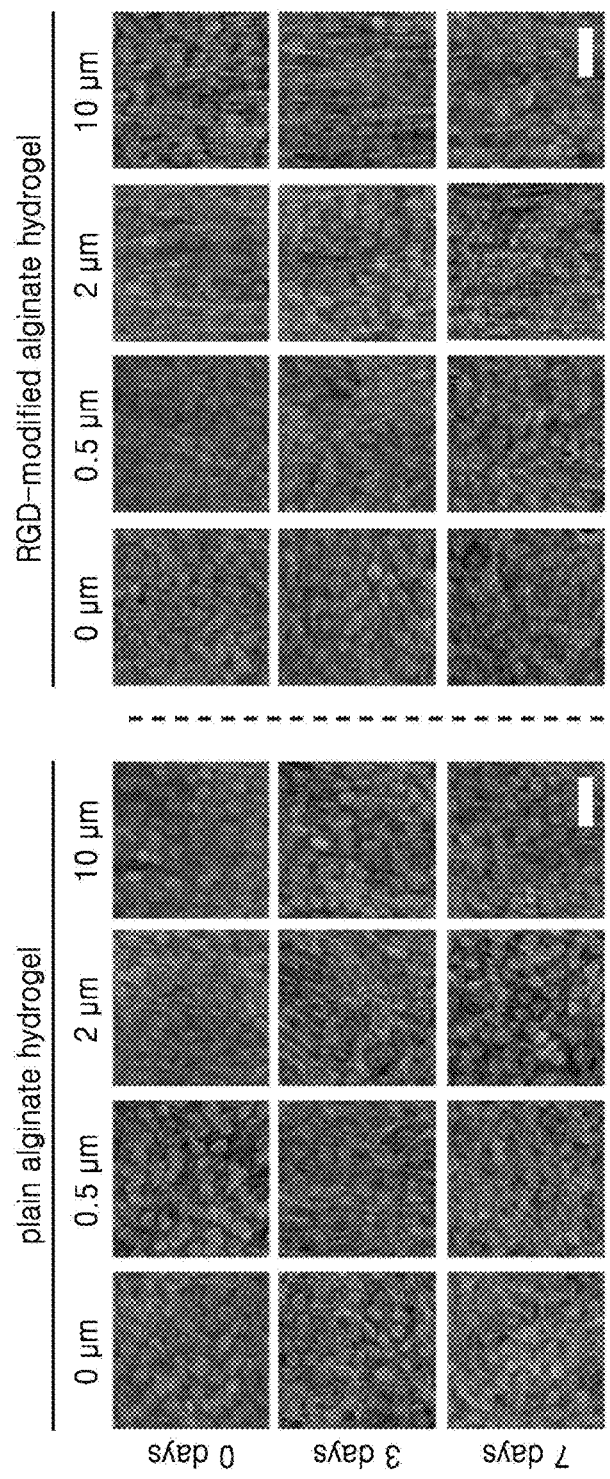
FIG. 5 shows microscope images obtained via immunostaining of the stamped cells which were removed from the alginate hydrogels having a pattern used to obtain the stamped cells and then incubated for 0 days, 3 days, or 7 days.

The fixed cells were stained using a cytoskeleton staining reagent and observed using a fluorescent microscope. The fluorescent microscope images of the stained cells are shown in FIG. 5 (White bar length: 50 μm). Referring to FIG. 5, the cells stamped on the plain alginate hydrogel or RGD-modified alginate hydrogel were found to stay aligned even after 7 days had passed from removal of the alginate hydrogel. Accordingly, it was found that a cell pattern obtained using alginate hydrogel having a pattern may be maintained even after the alginate hydrogel is removed.

It was also found that even when additional cell stamping was performed by adding an alginate hydrogel onto the previously stamped cells from which the alginate hydrogel had been removed, in a direction different from a previous stamping direction, the orientation or alignment and shape of the cells were rearranged.

The invention claimed is:

1. A cell patterning material comprising:
a chamber comprising a microporous membrane at the lower portion; and
a patterned biocompatible polymer hydrogel adhered to a lower surface of the microporous membrane;
wherein the lower portion of the biocompatible polymer hydrogel contacts an upper portion of a cell.

2. The cell patterning material of claim 1, wherein the biocompatible polymer hydrogel has a pattern of grooves and ridges; and
wherein each groove and each ridge of the biocompatible polymer hydrogel have a width of about 0.1 µm to about 50 µm and a width of about 0.1 µm to about 50 µm, respectively, and a height between each groove and each ridge is about 0.1 µm to about 50 µm.

3. The cell patterning material of claim 2, wherein the height between each groove and each ridge is about 0.1 µm to about 20 µm.

4. The cell patterning material of claim 1, wherein the biocompatible polymer hydrogel is an alginate hydrogel.

5. The cell patterning material of claim 4, wherein the alginate of the alginate hydrogel includes a polypeptide having an amino acid sequence of arginine-glycine-aspartic acid (Arg-Gly-Asp: RGD) from the N-terminus thereof.

6. A method of preparing the cell patterning material of claim 1, the method comprising:
adding a biocompatible polymer solution onto a polymer mold having a pattern;
contacting the biocompatible polymer solution on the polymer mold with the lower surface of the microporous membrane present at the lower portion of the chamber;
adding a calcium solution into the chamber to gelate the biocompatible polymer solution into a biocompatible polymer hydrogel having the pattern of the polymer mold; and
separating the patterned biocompatible polymer hydrogel adhered to the lower surface of the microporous membrane present at the lower portion of the chamber and the polymer mold from one another.

7. The method of claim 6, wherein the polymer mold has a pattern of grooves and ridges which are transferred to the patterned biocompatible hydrogel; wherein each groove and each ridge of the biocompatible polymer hydrogel have a width of about 0.1 µm to about 50 µm and a width of about 0.1 µm to about 50 µm, respectively, and a height between each groove and each ridge is about 0.1 µm to about 50 µm.

8. The method of claim 6, wherein the polymer mold comprises alkylsiloxane, polystyrene, polyacrylamide, polylactic acid, polyhydroxy acid, polyamide, polyamino acid, polyacetal, polycyanoacrylate, polyurethane, polypyrrole, polyester, polymethacrylate, polyethylene, polycarbonate, polyepoxyethane, or a combination thereof.

9. The method of claim 8, wherein the alkylsiloxane is polydimethylsiloxane (PDMS).

10. The method of claim 6, wherein the biocompatible polymer is alginate.

11. The method of claim 10, wherein the alginate includes an amino acid sequence of arginine-glycine-aspartic acid (Arg-Gly-Asp: RGD) from the N-terminus thereof.

12. The method of claim 6, wherein the calcium solution is a $CaCl_2$ solution, a $CaSO_4$ solution, or a $CaCO_3$ solution.

13. A cell patterning method comprising:
contacting cells with the cell patterning material of claim 1 to obtain patterned cells;
adding a biocompatible polymer lyase or a calcium-chelating agent to the chamber of the cell patterning material to remove the biocompatible polymer hydrogel; and
separating the patterned cells and the chamber from one another.

14. The cell patterning method of claim 13, wherein the cells are muscle cells, nerve cells, stem cells, connective tissue cells, vascular cells, or epithelial cells.

15. The cell patterning method of claim 13, wherein the contacting of the cells with the cell patterning material is performed for about 1 second to about 24 seconds.

16. The cell patterning method of claim 13, wherein the calcium-chelating agent is citrate, ethylenediaminetetraacetic acid (EDTA), ethyleneglycol tetraacetic acid (EGTA), BAPTA-AM, or a combination thereof.

17. The cell patterning method of claim 13, further comprising an incubation step after the adding of the biocompatible polymer lyase or the calcium-chelating agent to the chamber.

18. The cell patterning method of claim 13, further comprising contacting the patterned cells with the cell patterning material in a different direction from a contacting direction in claim 13 to change a patterning direction of the patterned cells.

* * * * *